(12) United States Patent
Terui et al.

(10) Patent No.: US 10,779,777 B2
(45) Date of Patent: Sep. 22, 2020

(54) RADIOGRAPHIC IMAGING APPARATUS, CONTROL METHOD THEREOF, AND COMPUTER-READABLE STORAGE MEDIUM

(71) Applicant: CANON KABUSHIKI KAISHA, Tokyo (JP)

(72) Inventors: Kosuke Terui, Yokohama (JP); Atsushi Iwashita, Tokyo (JP); Sho Sato, Tokyo (JP); Yoshiaki Ishii, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 203 days.

(21) Appl. No.: 16/032,384

(22) Filed: Jul. 11, 2018

(65) Prior Publication Data

US 2018/0317868 A1    Nov. 8, 2018

Related U.S. Application Data

(63) Continuation of application No. PCT/JP2016/084985, filed on Nov. 25, 2016.

(30) Foreign Application Priority Data

Jan. 27, 2016    (JP) ................. 2016-013831

(51) Int. Cl.
*A61B 6/00* (2006.01)
*G06T 5/00* (2006.01)
*A61B 6/03* (2006.01)

(52) U.S. Cl.
CPC ............ *A61B 6/4233* (2013.01); *A61B 6/032* (2013.01); *A61B 6/4241* (2013.01); *A61B 6/482* (2013.01);

(Continued)

(58) Field of Classification Search
CPC ..... A61B 6/4233; A61B 6/032; A61B 6/4241; A61B 6/482; A61B 6/585; G06T 5/002; G06T 5/005; G06T 2207/10116
See application file for complete search history.

(56) References Cited

U.S. PATENT DOCUMENTS 8,829,438 B2    9/2014    Sato et al.
9,048,154 B2    6/2015    Takenaka et al.
(Continued)

FOREIGN PATENT DOCUMENTS

JP    H08-304551 A    11/1996
JP    2001-194460 A    7/2001
(Continued)

OTHER PUBLICATIONS

U.S. Appl. No. 15/751,600, Yoshiaki Ishii, filed Feb. 9, 2018.
U.S. Appl. No. 15/969,842, Jun Kawanabe, filed May 3, 2018.
U.S. Appl. No. 16/045,127, Sho Sato, filed Jul. 25, 2018.

*Primary Examiner* — Christine S. Kim
(74) *Attorney, Agent, or Firm* — Venable LLP

(57) ABSTRACT

A radiographic imaging apparatus is provided. The apparatus comprises a sensor panel in which pixels are provided and a processor that generates an image that corresponds to the number of radiation photons incident on each of the pixels. In an imaging mode in which an image formed by radiation that has passed through a subject is generated, the processor generates a correction signal by correcting a value of a signal output from the conversion element of each of the pixels according to a correction coefficient for converting the value of the signal output from the conversion element on which a radiation photon was incident to a value that corresponds to an energy value of the radiation photon, and generates an image based on the number of correction (Continued)

signals of pixels on which a radiation photon was incident from among the correction signals of the pixels.

16 Claims, 12 Drawing Sheets

(52) U.S. Cl.
CPC .............. *A61B 6/585* (2013.01); *G06T 5/002* (2013.01); *G06T 5/005* (2013.01); *G06T 2207/10116* (2013.01)

(56) References Cited

U.S. PATENT DOCUMENTS

| | | | |
|---|---|---|---|
| 9,128,196 | B2 | 9/2015 | Sato et al. |
| 9,134,432 | B2 | 9/2015 | Iwashita et al. |
| 9,234,966 | B2 | 1/2016 | Sugawara et al. |
| 9,423,512 | B2 | 8/2016 | Sato et al. |
| 9,445,030 | B2 | 9/2016 | Yagi et al. |
| 9,456,790 | B2 | 10/2016 | Taguchi et al. |
| 9,462,989 | B2 | 10/2016 | Takenaka et al. |
| 9,468,414 | B2 | 10/2016 | Ryu et al. |
| 9,470,800 | B2 | 10/2016 | Iwashita et al. |
| 9,470,802 | B2 | 10/2016 | Okada et al. |
| 9,541,653 | B2 | 1/2017 | Iwashita et al. |
| 9,655,586 | B2 | 5/2017 | Yagi et al. |
| 9,743,018 | B2 | 8/2017 | Iwashita et al. |
| 9,812,474 | B2 | 11/2017 | Yagi et al. |
| 9,971,046 | B2 | 5/2018 | Ryu et al. |
| 9,980,685 | B2 | 5/2018 | Iwashita et al. |
| 9,989,656 | B2 | 6/2018 | Sato et al. |
| 10,009,990 | B2 | 6/2018 | Takenaka et al. |
| 2005/0238249 | A1 | 10/2005 | Okamura |
| 2011/0317054 | A1 | 12/2011 | Kameshima et al. |
| 2014/0239186 | A1 | 8/2014 | Sato et al. |
| 2014/0361189 | A1 | 12/2014 | Kameshima et al. |
| 2016/0134818 | A1* | 5/2016 | Iwashita .............. A61B 6/4233 348/162 |
| 2016/0270755 | A1 | 9/2016 | Takenaka et al. |
| 2016/0374629 | A1* | 12/2016 | Kawata .................. A61B 6/032 378/19 |
| 2018/0070906 | A1 | 3/2018 | Terui et al. |
| 2018/0128755 | A1 | 5/2018 | Iwashita et al. |
| 2018/0136343 | A1 | 5/2018 | Terui et al. |

FOREIGN PATENT DOCUMENTS

| | | |
|---|---|---|
| JP | 2005-304818 A | 11/2005 |
| JP | 2011-085479 A | 4/2011 |
| JP | 2015-019157 A | 1/2015 |
| JP | 2015-062657 A | 4/2015 |
| JP | 2015-184116 A | 10/2015 |
| WO | WO-2015005262 A1 * | 1/2015 ............... H04N 5/32 |

* cited by examiner

CORRECTION COEFFICIENT IMAGE

F I G. 7A
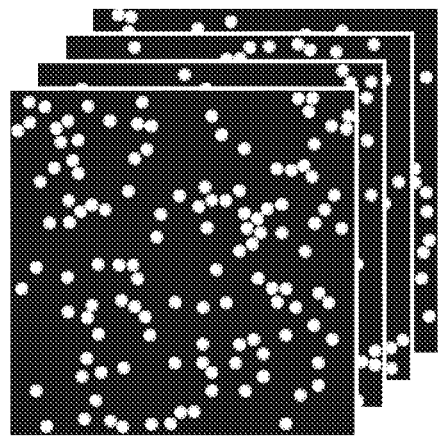
F I G. 7B
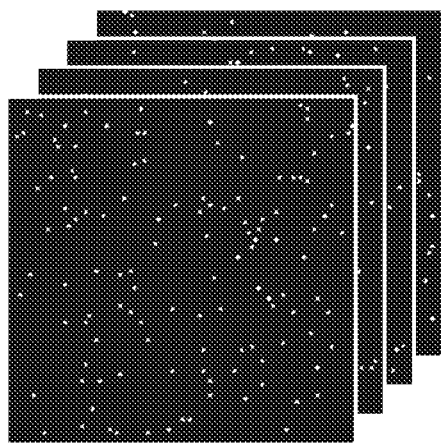
F I G. 7C
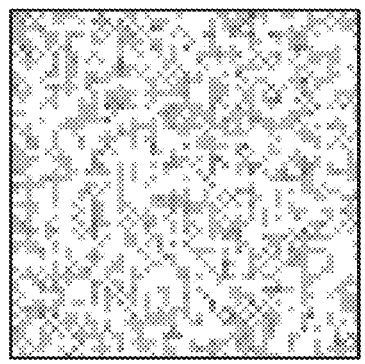
CORRECTION
COEFFICIENT IMAGE

RADIOGRAPHIC IMAGING APPARATUS, CONTROL METHOD THEREOF, AND COMPUTER-READABLE STORAGE MEDIUM

CROSS-REFERENCE TO RELATED APPLICATIONS

This application is a Continuation of International Patent Application No. PCT/JP2016/084895, filed Nov. 25, 2016, which claims the benefit of Japanese Patent Application No. 2016-013831, filed Jan. 27, 2016, both of which are hereby incorporated by reference herein in their entirety.

BACKGROUND OF THE INVENTION

Field of the Invention

The present invention relates to a radiographic imaging apparatus, a control method thereof, and a computer-readable storage medium.

Description of the Related Art

As an imaging apparatus for use in medical imaging diagnostic and non-destructive inspection that use radiation, a radiographic imaging apparatus is known that includes a flat panel detector (hereinafter referred to as FPD) made of a semiconductor material. Such a radiographic imaging apparatus may be used as a digital imaging apparatus for capturing a still image, a moving image or the like in, for example, medical imaging diagnostic.

An integral sensor is widely known that measures the total amount of electric charges generated by incidence of radiation as a radiation detection method for use in an FPD. As another type of sensor, there is a photon-counting sensor that measures the number of incident radiation photons. Japanese Patent Laid-Open No. 2011-85479 discloses a direct photon-counting sensor in which radiation photons are directly detected by each pixel using CdTe or the like. Japanese Patent Laid-Open No. 2001-194460 discloses an indirect photon-counting sensor in which incident radiation photons are converted to light by a scintillator, and the light obtained through the conversion of radiation is detected by each pixel.

In an FPD in which a plurality of pixels, each including a photon-counting sensor, are provided, if the sensitivity to incident radiation photons varies from pixel to pixel, the resulting radiographic image has poor image quality. In order to improve the image quality of the radiographic image, it is necessary to correct the variation in sensitivity to radiation photons between pixels. Japanese Patent Laid-Open No. 2011-85479 discloses that sensitivity correction is performed using a count value obtained by counting incident radiation photons. However, the accuracy of correction may decrease if the intensity of incident radiation photons is not uniform throughout the plane of the FPD. Also, Japanese Patent Laid-Open No. 2001-194460 is silent on sensitivity correction.

Some embodiments of the present invention provide a technique for, in a radiographic imaging apparatus that uses a photon-counting sensor, suppressing image degradation caused by a variation in sensitivity between pixels.

SUMMARY OF THE INVENTION

According to some embodiments, a radiographic imaging apparatus comprising: a sensor panel in which a plurality of pixels are provided, each pixel including a conversion element for detecting radiation; and a processor that generates an image that corresponds to the number of radiation photons incident on each of the plurality of pixels, wherein, in an imaging mode in which an image formed by radiation that has passed through a subject is generated, the processor generates a correction signal by correcting a value of a signal output from the conversion element of each of the plurality of pixels according to a correction coefficient for converting the value of the signal output from the conversion element on which a radiation photon was incident to a value that corresponds to an energy value of the radiation photon, and generates an image based on the number of correction signals of pixels on which a radiation photon was incident from among the correction signals of the plurality of pixels, is provided.

According to some other embodiments, a control method for controlling a radiographic imaging apparatus including a sensor panel in which a plurality of pixels are provided, each pixel including a conversion element for detecting radiation, the control method comprising: in order to form an image formed by radiation that has passed through a subject, generating a correction signal by correcting a value of a signal output from the conversion element of each of the plurality of pixels according to a correction coefficient for converting a value of a first signal output from the conversion element on which a radiation photon was incident to a value that corresponds to an energy value of the radiation photon; and generating an image based on the number of correction signals of pixels on which a radiation photon was incident from among the correction signals of the plurality of pixels, is provided.

According to some other embodiments, a non-transitory computer-readable storage medium storing a program for causing a computer to execute a control method for controlling a radiographic imaging apparatus including a sensor panel in which a plurality of pixels are provided, each pixel including a conversion element for detecting radiation, the control method comprising: in order to form an image formed by radiation that has passed through a subject, generating a correction signal by correcting a value of a signal output from the conversion element of each of the plurality of pixels according to a correction coefficient for converting a value of a first signal output from the conversion element on which a radiation photon was incident to a value that corresponds to an energy value of the radiation photon; and generating an image based on the number of correction signals of pixels on which a radiation photon was incident from among the correction signals of the plurality of pixels, is provided.

Further features of the present invention will become apparent from the following description of exemplary embodiments with reference to the attached drawings.

BRIEF DESCRIPTION OF THE DRAWINGS

The accompanying drawings are included in the specification as a part thereof, and are used to illustrate the embodiments of the present invention and describe the principle of the present invention together with the description contained in the specification.

FIGS. 7A to 7C are diagrams showing a method for acquiring a correction coefficient image performed in the radiographic imaging apparatus shown in FIG. 1.

DESCRIPTION OF THE EMBODIMENTS

Hereinafter, specific embodiments of the radiographic imaging apparatus according to the present invention will be described with reference to the accompanying drawings. It is to be noted that in the present invention, the term "radiation" may include α rays, β rays, γ rays, and the like that are beams that produce particles (including photons) emitted from a radioactive decay, as well as beams that have a similar or higher level of energy such as, for example, X rays, particle rays, and cosmic rays.

Figure 1:
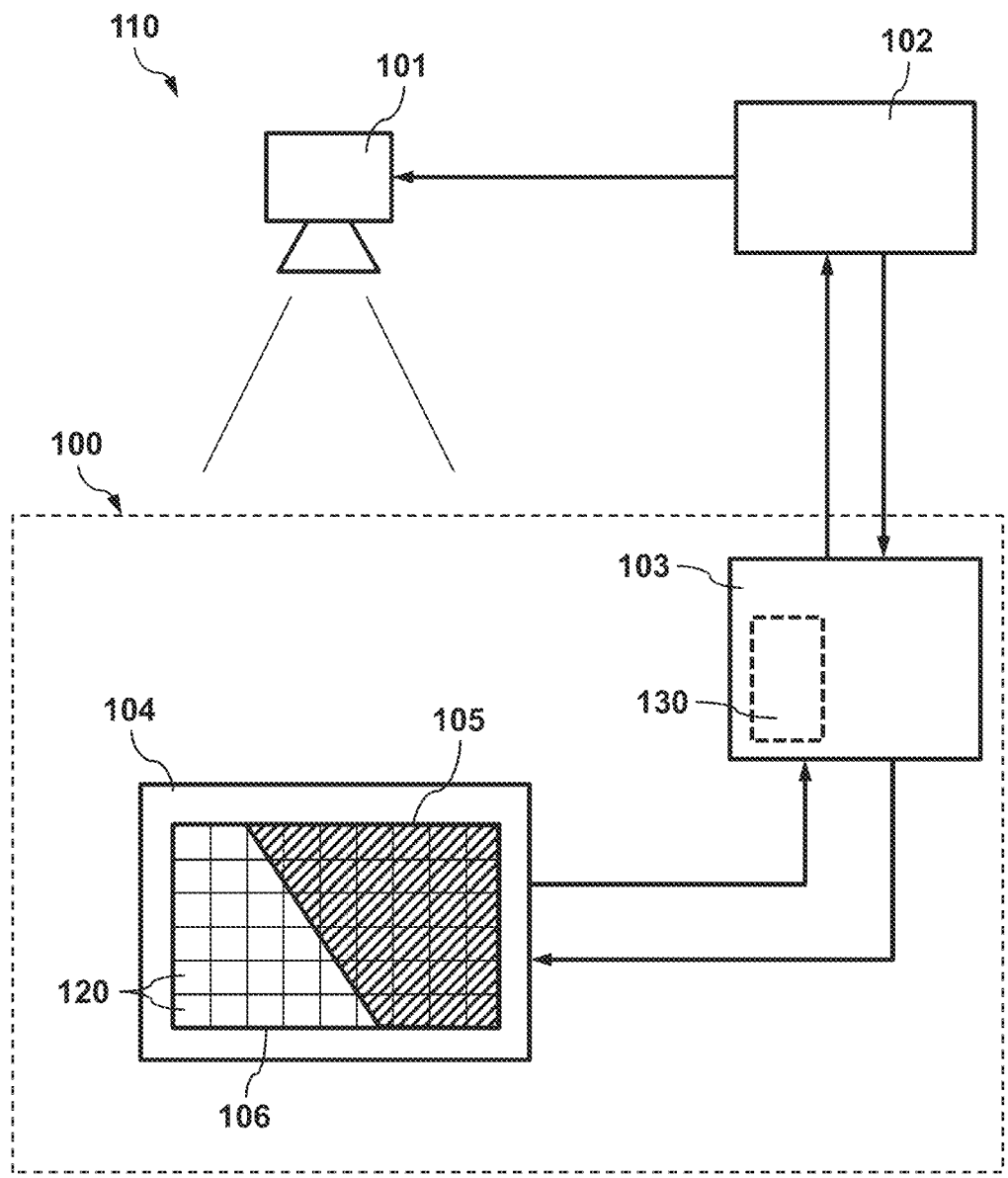
FIG. 1 is a diagram showing a configuration example of a radiographic imaging apparatus according to the present invention.

A radiographic imaging apparatus according to an embodiment of the present invention will be described with reference to FIGS. 1 to 9. FIG. 1 shows a configuration example of a radiographic imaging apparatus 100 according to a first embodiment of the present invention. The radiographic imaging apparatus 100 includes an imaging portion 104 that captures a radiographic image, and a processor 103. The radiographic imaging apparatus 100 may constitute a radiographic imaging system 110, together with a radiation source 101 that irradiates the radiographic imaging apparatus 100 with radiation, and an irradiation controller 102 that controls the radiation source 101. The irradiation controller 102 and the processor 103 may be implemented by computers or the like that include a CPU, a memory, and the like. In the present embodiment, the irradiation controller 102 and the processor 103 are provided separately, but the configuration is not limited thereto. For example, the irradiation controller 102 may be integrated with the processor 103, and included in the radiographic imaging apparatus 100. That is, the irradiation controller 102 and the processor 103 may be implemented by one computer that has the functions of the irradiation controller 102 and the processor 103.

The imaging portion 104 of the radiographic imaging apparatus 100 includes a sensor panel 106 that includes a scintillator 105 that converts incident radiation to light, and a plurality of pixels 120. The plurality of pixels 120 use the scintillator 105 in a shared manner. Each of the pixels 120 includes a photodetector that detects light generated through conversion of radiation by the scintillator 105. That is, in the present embodiment, in order to detect incident radiation, an indirect conversion element is used in which incident radiation is converted to light by the scintillator 105, and the light is converted to a signal that corresponds to the intensity of the light in a photodetector provided in each pixel 120 as a conversion element. On the sensor panel 106, a plurality of pixels 120 are provided in a two dimensional array so as to form a plurality of rows and a plurality of columns. Each of the photodetectors included in the pixels 120 outputs, to the processor 103, a signal (optical signal) that has a value that corresponds to the intensity of light generated through conversion of radiation photons incident on the sensor panel 106 by the scintillator 105. The intensity of light generated through conversion by the scintillator 105 varies according to the energy of each individual radiation photon of incident radiation, and thus the value of a signal output from the photodetector provided in each pixel 120 may be a signal value that corresponds to the energy of incident radiation photon. The radiographic imaging apparatus 100 has a configuration for performing photon-counting radiographic imaging, and counts the number of incident radiation photons based on the result of detection of light.

The processor 103 performs transmission and reception of signals and data with respect to the imaging portion 104. To be specific, the processor 103 captures a radiographic image by controlling the imaging portion 104, and receives a signal obtained by capturing the radiographic image from the imaging portion 104. The signal contains a radiation photon-count value. For example, the processor 103 generates, based on the count value, image data for displaying an image captured by radiation on, for example, a display portion (not shown) such as a display (not shown). At this time, the processor 103 may perform predetermined correction processing on the image data. The correction processing will be described later. Also, the processor 103 may supply a signal for starting or ending irradiation with radiation to the irradiation controller 102.

Figure 2:
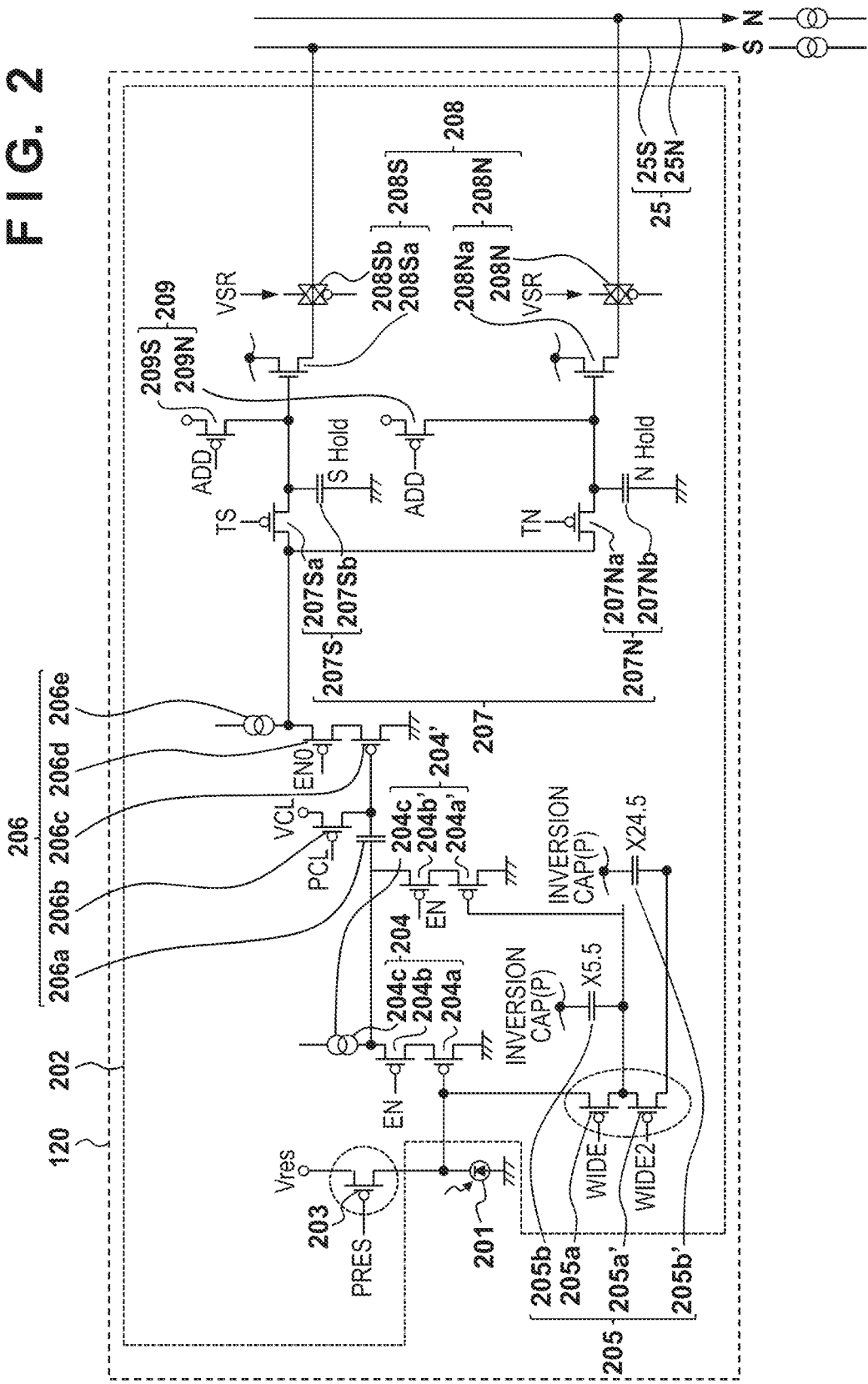
FIG. 2 is a diagram showing a configuration of a pixel included in the radiographic imaging apparatus shown in FIG. 1.

FIG. 2 shows an equivalent circuit of a pixel 120 included in the sensor panel 106 according to the present embodiment. The pixel 120 may include a photoelectric conversion element 201 that serves as a photodetector that detects light generated through conversion of radiation photons by the scintillator 105, and an output circuit portion 202. Typically, the photoelectric conversion element 201 may be a photo diode. The output circuit portion 202 may include an amplifier circuit portion 204, a clamp circuit portion 206, a sample hold circuit portion 207, and a selection circuit portion 208.

The photoelectric conversion element 201 includes an charge accumulation portion. The charge accumulation portion is connected to the gate of a MOS transistor 204a included in the amplifier circuit portion 204. The source of the MOS transistor 204a is connected to a current source 204c via a MOS transistor 204b. A source follower circuit is formed by the MOS transistor 204a and the current source 204c. The MOS transistor 204b is an enable switch that is turned on when an enable signal EN supplied to its gate is set to an active level, and enables the source follower circuit to operate.

In the example shown in FIG. 2, the charge accumulation portion of the photoelectric conversion element 201 and the gate of the MOS transistor 204a constitute a common node. The node functions as a charge-voltage converter that converts electric charges accumulated in the charge accumulation portion to a voltage. That is, in the charge-voltage converter, a voltage V ($=Q/C$) appears, the voltage V being determined by electric charges Q accumulated in the charge accumulation portion and a capacitance value C of the charge-voltage converter. The charge-voltage converter is connected to a reset potential Vres via a reset switch 203. When a reset signal PRES is set to an active level, the reset switch 203 is turned on, and the potential of the charge-voltage converter is reset to the reset potential Vres.

A clamp circuit portion 206 clamps, by using a clamp capacitor 206a, noise that is output by the amplifier circuit portion 204 according to the reset potential of the charge-voltage converter. That is, the clamp circuit portion 206 is a circuit for cancelling the noise from the signal output from the source follower circuit according to the electric charges generated by the photoelectric conversion element 201 through photoelectric conversion. The noise may contain kTC reset noise. Clamping is performed by setting a clamp signal PCL to an active level so as to turn on a MOS transistor 206b, and thereafter setting the clamp signal PCL to an inactive level so as to turn off the MOS transistor 206b. The output terminal of the clamp capacitor 206a is connected to the gate of a MOS transistor 206c. The source of the MOS transistor 206c is connected to a current source 206e via a MOS transistor 206d. A source follower circuit is formed by the MOS transistor 206c and the current source 206e. The MOS transistor 206d is an enable switch that is turned on when an enable signal EN0 supplied to its gate is set to an active level, and enables the source follower circuit to operate.

A signal output from the clamp circuit portion 206 according to the electric charges generated by the photoelectric conversion element 201 through photoelectric conversion is written, as an optical signal, into a capacitor 207Sb via a switch 207Sa in response to an optical signal sampling signal TS being set to an active level. The signal output from the clamp circuit portion 206 when the MOS transistor 206b is turned on immediately after the potential of the charge-voltage converter is reset is a clamp voltage. This noise signal is written into a capacitor 207Nb via a switch 207Na in response to a noise sampling signal TN being set to an active level. The noise signal contains an offset component of the clamp circuit portion 206. A signal sample hold circuit 207S is formed by the switch 207Sa and the capacitor 207Sb, and a noise sample hold circuit 207N is formed by the switch 207Na and the capacitor 207Nb. The sample hold circuit portion 207 includes the signal sample hold circuit 207S and the noise sample hold circuit 207N.

When a driving circuit portion (not shown) drives a row selection signal VSR to an active level, a signal (optical signal) stored in the capacitor 207Sb is output to a signal line 25S via a MOS transistor 208Sa and a row selection switch 208Sb. Also, at the same time, a signal (noise) stored in the capacitor 207Nb is output to a signal line 25N via a MOS transistor 208Na and a row selection switch 208Nb. The MOS transistor 208Sa constitutes a source follower circuit together with a constant current source (not shown) provided on the signal line 25S. Likewise, the MOS transistor 208Na constitutes a source follower circuit together with a constant current source (not shown) provided on the signal line 25N. A signal selection circuit portion 208S is formed by the MOS transistor 208Sa and the row selection switch 208Sb, and a noise selection circuit portion 208N is formed by the MOS transistor 208Na and the row selection switch 208Nb. The selection circuit portion 208 includes the signal selection circuit portion 208S and the noise selection circuit portion 208N.

The pixel 120 may include a summation switch 209S that sums the optical signals of a plurality of adjacent pixels 120. In a summation mode, a summation mode signal ADD is set to an active level, and the summation switch 209S is turned on. In response thereto, the capacitors 207Sb of the adjacent pixels are connected to each other by the summation switch 209S, and the optical signals are averaged. Likewise, the pixel 120 may include a summation switch 209N that sums the noise of a plurality of adjacent pixels 120. When the summation switch 209N is turned on, the capacitors 207Nb of the adjacent pixels are connected to each other by the summation switch 209N, and the noise is averaged. A summation portion 209 includes the summation switch 209S and the summation switch 209N.

The pixel 120 may include a sensitivity changing portion 205 for changing sensitivity. The pixel 120 may include, for example, a first sensitivity changing switch 205a, a second sensitivity changing switch 205a', and a circuit element that is attached thereto. When a first change signal WIDE is set to an active level, the first sensitivity changing switch 205a is turned on, and the capacitance value of a first additional capacitor 205b is added to the capacitance value of the charge-voltage converter. As a result, the sensitivity of the pixel 120 decreases. When a second change signal WIDE2 is set to an active level, the second sensitivity changing switch 205a' is turned on, and the capacitance value of a second additional capacitor 205b' is added to the capacitance value of the charge-voltage converter. As a result, the sensitivity of the pixel 120 further decreases. By adding the above function that causes the sensitivity of the pixel 120 to decrease, it is possible to receive a larger amount of light, and expand the dynamic range. A configuration is also possible in which, when the first change signal WIDE is set to an active level, an enable signal ENw is set to an active level, and instead of the MOS transistor 204a, a MOS transistor 204a' is caused to operate as a source follower.

The optical signal output from the circuit included in the pixel 120 as described above may be converted to a digital value by an AD converter (not shown), and thereafter supplied to the processor 103. The processor 103 processes the optical signal as a signal output from each pixel 120.

Figure 3:
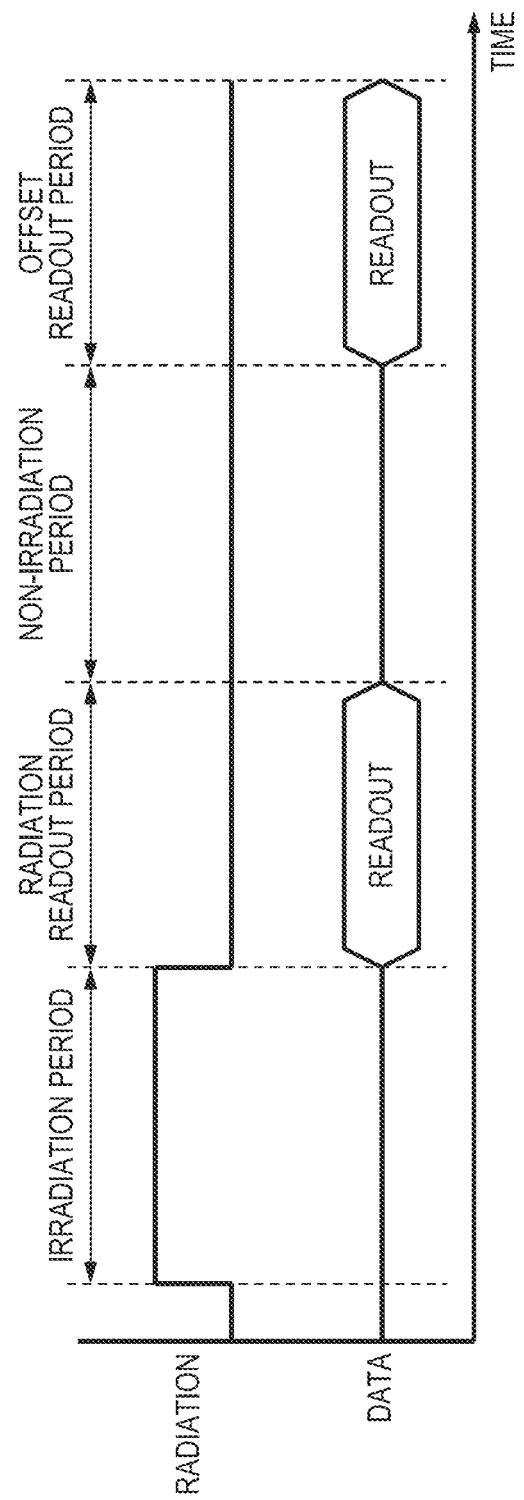
FIG. 3 is a diagram showing an irradiation period and a readout period for a sensor panel included in the radiographic imaging apparatus shown in FIG. 1.

Next, driving of the radiographic imaging apparatus 100 according to the present embodiment will be described. FIG. 3 is a diagram showing a drive timing of the radiographic imaging apparatus 100. The waveform shown in FIG. 3 indicates an irradiation period, and a readout period during which data DATA is read out, with the horizontal axis representing time. In FIG. 3, the irradiation period is a period during which radiation is emitted from the radiation source 101. During this period, radiation incident on the sensor panel 106 is converted to light by the scintillator 105, and the photodetector of each pixel 120 outputs a signal that corresponds to the intensity of the light. Likewise, the readout period is a period during which data DATA obtained during the irradiation period is output from the sensor panel 106 to the processor 103. The radiographic imaging apparatus 100 acquires a still image or a moving image by alternately performing the irradiation period and the radiation readout period. Also, the radiographic imaging apparatus 100 according to the present embodiment acquires a still image or a moving image through an irradiation period, a radiation readout period, a non-irradiation period, and an offset readout period that constitute one frame. The radiographic imaging apparatus 100 can correct unnecessary offset information by subtracting a signal value acquired during offset readout period from a signal value acquired during the radiation readout period.

Figure 4A:
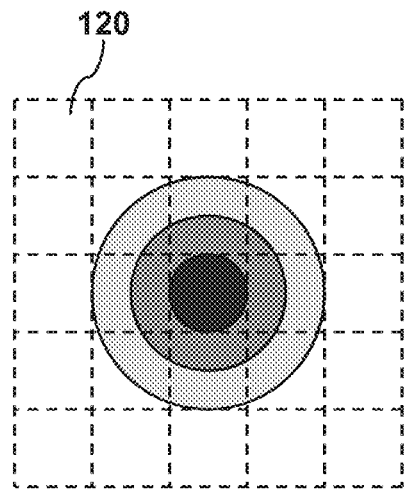
FIGS. 4A to 4C are diagrams showing first processing performed in the radiographic imaging apparatus shown in FIG. 1.
Figure 4B:
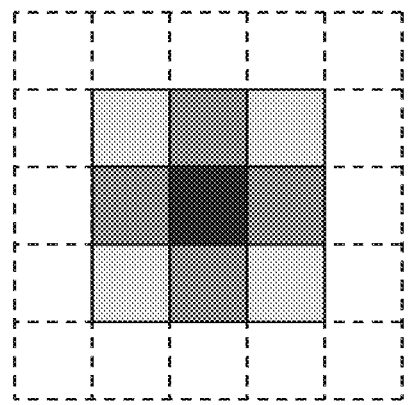
Figure 4C:
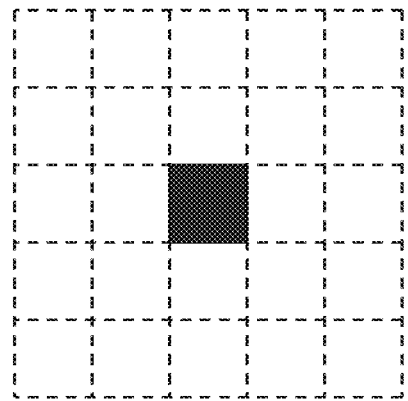

Next, a description will be given of a first processing method in which determination of a pixel 120 that is at the position at which a radiation photon was incident in the sensor panel 106 and correction of the value of a signal output from the photodetector of the pixel 120 according to the intensity of light generated through conversion of the incident radiation photon by the scintillator 105 are performed, with reference to FIGS. 4A to 4C. In the sensor panel 106 that includes indirect conversion elements that use the scintillator 105 so as to detect incident radiation photons, the light generated through conversion of a radiation photon by the scintillator 105 diffuses within the scintillator 105, and may be detected by the photodetectors of a plurality of pixels 120. For example, the light generated from one radiation photon is detected by a plurality of pixels 120 as shown in FIG. 4A. At this time, an image generated by the signals output from the photodetectors of the pixels 120 is an image as shown in, for example, FIG. 4B. In this specification, an image as shown in FIG. 4B obtained based on the light generated through conversion of one radiation photon by the scintillator 105 is defined as a light emission image. The processor 103 analyzes the light emission image, thereby determines a pixel 120 above which the radiation photon was incident on the scintillator 105, and corrects the signal value output from the photodetector of the pixel 120 according to the position at which the radiation photon was incident.

As a method for determining the position of a pixel on which a radiation photon was incident, first, the processor 103 determines whether the value of a signal output from each pixel 120 is greater than a predetermined value. This value may be a threshold value for determining whether or not the light generated by the scintillator 105 through conversion of a radiation photon incident on the sensor panel 106 has been detected by each pixel 120.

Next, the processor 103 identifies, from among the pixels 120, a group of pixels 120 that have output signals indicating the incidence of light generated through conversion of a radiation photon during the same period (frame). The group is composed of a plurality of pixels 120 that are adjacent to each other and have output signals indicating the detection of the light during the same period.

After a group of pixels 120 has been identified, the processor 103 determines a pixel 120 above which the radiation photon was incident on the scintillator 105 from among the pixels 120 included in the group based on the distribution of the group. In the present embodiment, the photodetector of each pixel 120 outputs a signal that has a value that corresponds to the intensity of incident light. For this reason, the processor 103 may determine, for example, one of the pixels 120 included in the group that has output the highest signal value from its photodetector, as the pixel 120 that is at the position at which a radiation photon was incident. Alternatively, for example, the processor 103 may determine, based on the arrangement of the pixels 120 of the group on the sensor panel 106, a pixel 120 that is at a geometric barycenter position as the pixel 120 that is at the position at which a radiation photon was incident. Alternatively, for example, distribution patterns of light emission images at the time of incidence of a radiation photon may be stored in advance in a memory 130 provided in the processor 103. In this case, the processor 103 may determine the pixel 120 that is at the position at which a radiation photon was incident by pattern matching the light emission image of the group.

After a pixel 120 that is at the position at which a radiation photon was incident has been determined, the processor 103 corrects the value of a signal from the photodetector of each pixel 120 included in the group according to the position at which the radiation photon was incident. For example, the processor 103 may perform correction by summing the values of signals output from the photodetectors of the pixels 120 included in the group, and using the summed value as the signal value of the pixel 120 that is at the position at which a radiation photon was incident. Alternatively, for example, the processor 103 may perform correction by summing the signal value of the pixel 120 that has been determined as the pixel 120 that is at the position at which a radiation photon was incident, and the signal values of adjacent pixels 120 that are adjacent to the pixel 120, and using the summed value as the signal value output from the pixel 120 that is at the position at which a radiation photon was incident. Alternatively, the processor 103 may perform correction by setting the values of signals from the photodetectors of pixels 120 in the group other than the pixel 120 that has been determined as the pixel 120 that is at the position at which a radiation photon was incident to the same value such as that of a signal when light is not detected. Alternatively, for example, in the case where the pixel 120 that is at the position at which a radiation photon was incident is determined through pattern matching, corrected signal values may be stored in addition to the light emission images stored in the memory 130, and the processor 103 may correct signal values based on the stored values. As a result, an image as shown in FIG. 4C is generated in which a pixel that is at the position at which a radiation photon was incident has been determined, and signal correction has been performed to correspond to the energy of the incident radiation photon. In this specification, the image shown in FIG. 4C is defined as a radiation photon position determined image.

If none of adjacent pixels 120 that are adjacent to one pixel 120 that has output a signal indicating that light has been detected detects light, the one pixel 120 is determined as the pixel 120 that is at the position at which a radiation photon was incident, and the need for correcting the signal from this pixel 120 may be low. For this reason, if none of adjacent pixels 120 that are adjacent to one pixel 120 that has output a signal indicating that light has been detected detects light, the processor 103 does not need to perform first processing on the one pixel 120.

In the present embodiment, the sensor panel 106 that includes indirect conversion elements (photodetectors) that use the scintillator 105 is used. However, as the detection elements, it is also possible to use direct conversion elements that directly convert a radiation photon to a signal corresponding to the energy of the incident radiation photon. In the case where a sensor panel that includes direct conversion elements is used, the processor 103 may determine a pixel that has output a signal that has a value greater than a predetermined value as the pixel on which a radiation photon was incident. The sensor panel that includes direct conversion elements does not use a scintillator 105, and thus the possibility that light is diffused and detected by a plurality of pixels as in the sensor panel that includes indirect conversion elements is low. For this reason, the processor 103 may omit first processing when a sensor panel that includes direct conversion elements is used.

Figure 5A:
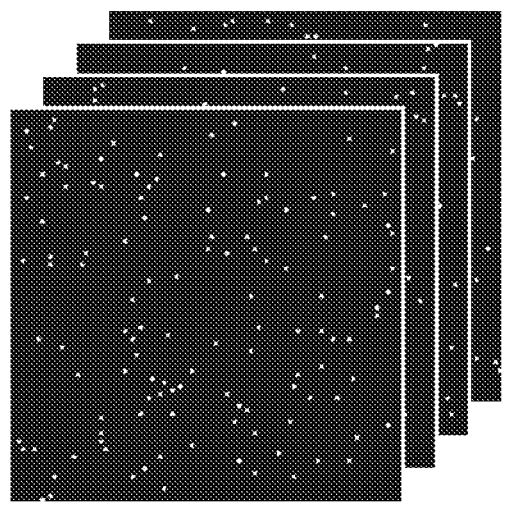
FIGS. 5A and 5B are diagrams showing a method for acquiring a captured radiographic image, performed in the radiographic imaging apparatus shown in FIG. 1.
Figure 5B:
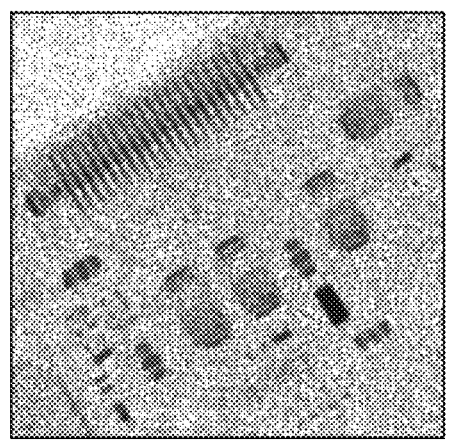

Next, a method for generating a radiographic image by using radiation photon position determined images is shown in FIGS. 5A and 5B. In an imaging mode in which an image formed by radiation that has passed through a subject is generated, radiation is emitted from the radiation source 101 to the subject. For example, when a plurality of frames are captured with the subject being fixed, the processor 103 reads out data DATA for each frame from the sensor panel 106. The readout data DATA is used by the processor 103 to perform the above-described first processing so as to determine the position of a pixel 120 that is at the position at which a radiation photon was incident, and correct the signal output from the photodetector of each pixel 120. Through this processing, a plurality of radiation photon position determined images per frame as shown in FIG. 5A are acquired. A radiographic image as shown in FIG. 5B can be generated from the plurality of radiation photon position determined images. As the method for generating a radiographic image, the processor 103 counts, for each pixel 120, the number of detections of the signal indicating that a radiation photon was incident, and generates a radiographic image as shown in FIG. 5B based on the counted number. Each bright spot in a radiation photon position determined image per frame shown in FIG. 5A indicates that the signal indicating that a radiation photon was incident was detected once in the pixel 120. The counted number obtained in each pixel 120 may be used as the pixel value of the pixel in the radiographic image. Alternatively, for example, the processor 103 may count, among the signals output from the photodetector of each pixel 120, a signal output each time a radiation photon is incident according to a plurality of levels based on the value of the signal. The processor 103 may generate a radiographic image based on the number of signals indicating that a radiation photon was incident that has been counted according to a plurality of levels. In this case, the processor 103 may change the output color according to the plurality of levels, and synthesize a color radiographic image that has a color corresponding to the energy of incident radiation photons. Through counting according to a plurality of levels based on the signal value, the radiographic imaging apparatus 100 attains energy resolution for incident radiation photons.

For the sake of simplification of the description, in FIG. 5A and subsequent drawings as well as the corresponding description, it is assumed that an image is generated for every frame. However, the processor 103 does not necessarily generate an image for every frame. A radiographic image is generated by counting, among the signals output from each pixel 120, the number of signals indicating that light generated through conversion of radiation has been detected.

Next, a description will be given of a method for correcting a radiographic image according to the present embodiment with reference to FIGS. 6A to 6D. The pixels 120 that are provided on the sensor panel 106 do not necessarily have a constant sensitivity to the energy of incident radiation. The pixels 120 may have different sensitivities to the energy of incident radiation photons due to, for example, a characteristics variation within the plane of the scintillator 105, and a variation in gain for light of the photodetector between pixels 120. Due to the differences in sensitivity, even if radiation photons that have the same energy are incident on the sensor panel 106, a signal that has a different value may be output from the photodetector of each pixel 120. Accordingly, the processor 103 corrects a value of a signal output from the photodetector of each pixel 120 according to a correction coefficient determined in a calibration mode, which will be described later, the correction coefficient being for converting the value of a signal output from the photodetector of each pixel 120 to a value that corresponds to the energy value of an incident radiation photon. The correction coefficient indicates sensitivity to radiation photons incident on each pixel 120. When the correction coefficient determined for each of the pixels 120 that are disposed on the sensor panel 106 is plotted on an image, a correction coefficient image as shown in FIG. 6D, which is a group of correction coefficients, is generated. The processor 103 corrects the value of a signal output from the photodetector of each pixel 120 according to the correction coefficient (correction coefficient image) so as to make the sensitivity uniform.

Figure 6A:
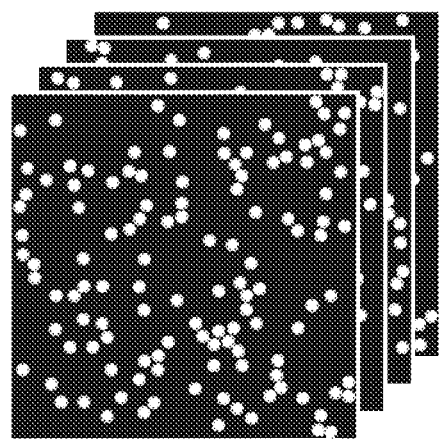
FIGS. 6A to 6D are diagrams showing a method for correcting a captured radiographic image, performed in the radiographic imaging apparatus shown in FIG. 1.
Figure 6B:
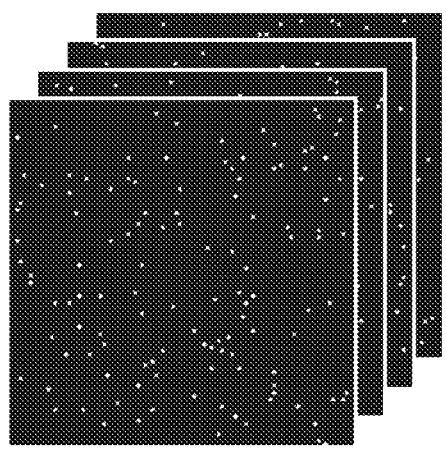
Figure 6C:
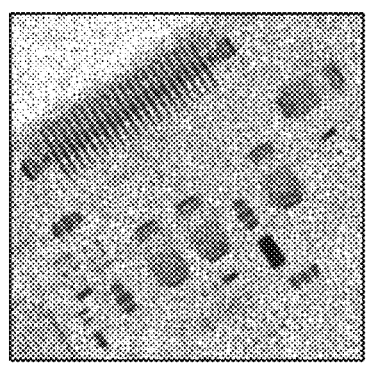
Figure 6D:
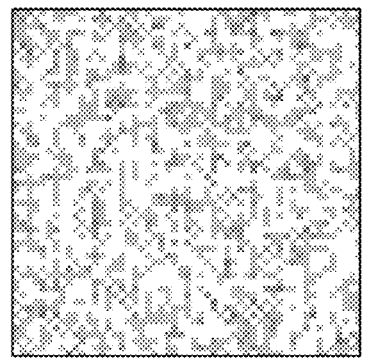

FIGS. 6A to 6C show a sequence in which the processor 103 corrects an image acquired for each frame according to the correction coefficients, and generates a radiographic image. FIG. 6A shows light emission images as shown in FIG. 4B acquired for each frame. FIG. 6B shows radiation photon position determined images generated from the light emission images shown in FIG. 6A through first processing. FIG. 6C shows a radiographic image generated from a plurality of radiation photon position determined images acquired for each frame. The correction according to the correction coefficients may be performed at any stage of FIGS. 6A to 6C, but it may be most effective to perform correction on the light emission images shown in FIG. 6A. The processor 103 performs correction on each signal value of a light emission image according to the correction coefficient, and generates a correction signal for each signal. Then, by performing first processing using the generated correction signals, the determination of the position of a pixel 120 on which a radiation photon was incident, and the correction of the value of a signal output from the photodetector provided in each pixel 120 may be performed more accurately. Accordingly, the information regarding the energy of radiation photons incident on each pixel 120 of the radiographic image generated from the radiation photon position determined images may become more accurate.

A method for acquiring the above-mentioned correction coefficient image will be described with reference to FIGS. 7A to 7C. In a calibration mode in which radiation that has a predetermined energy value is incident on the sensor panel 106 of the radiographic imaging apparatus 100, the processor 103 determines a correction coefficient for each pixel 120, and acquires a correction coefficient image. In order to cause radiation that has a predetermined energy value to be incident on the sensor panel, the calibration mode is performed without placing a subject between the radiation source 101 and the sensor panel 106.

First, the processor 103 acquires light emission images for a plurality of frames while radiation that has a predetermined energy value is incident. The processor 103 generates radiation photon position determined images shown in FIG. 7B from a plurality of light emission images shown in FIG. 7A by performing first processing. Next, in each radiation photon position determined image, the processor 103 acquires the value of a signal output from the photodetector of each pixel 120 on which a radiation photon was incident. Next, the processor 103 determines a correction coefficient based on the value of a signal from a pixel 120 on which a radiation photon was incident and a value that corresponds to when a radiation photon that has a predetermined energy value is incident. To be specific, the correction coefficient is determined by converting the value of a signal from the pixel 120 on which a radiation photon was incident to the value that corresponds to when a radiation photon that has a predetermined energy value is incident. As used herein, the term "value that corresponds to when a radiation photon that has a predetermined energy value is incident" may be a designed value of the signal output from the photodetector of each pixel 120 with respect to the energy value of the incident radiation photon. Also, the energy value of the radiation photon incident on the sensor panel 106 may be acquired, for example, from the irradiation controller 102 that controls the radiation source 101. A group of correction coefficients determined for each pixel 120 by the processor 103 is a correction coefficient image shown in FIG. 7C. Also, because the energy of an incident radiation photon has a predetermined value, a first signal that is acquired may be a value close to the designed value. By acquiring a value close to the designed value, it is possible to prevent a situation in which the correction coefficient is determined by noise caused by a radiation photon being not incident or an irregular signal, which will be described later.

In order to determine a correction coefficient for each pixel 120, the processor 103 needs to acquire, for each pixel 120, at least one signal output from the photodetector when a radiation photon is incident. Alternatively, the processor 103 may acquire, for each pixel 120, a plurality of signals output from the photodetector when a radiation photon is incident, and determine a correction coefficient of the pixel 120 based on a statistic of the plurality of signals.

Figure 8:
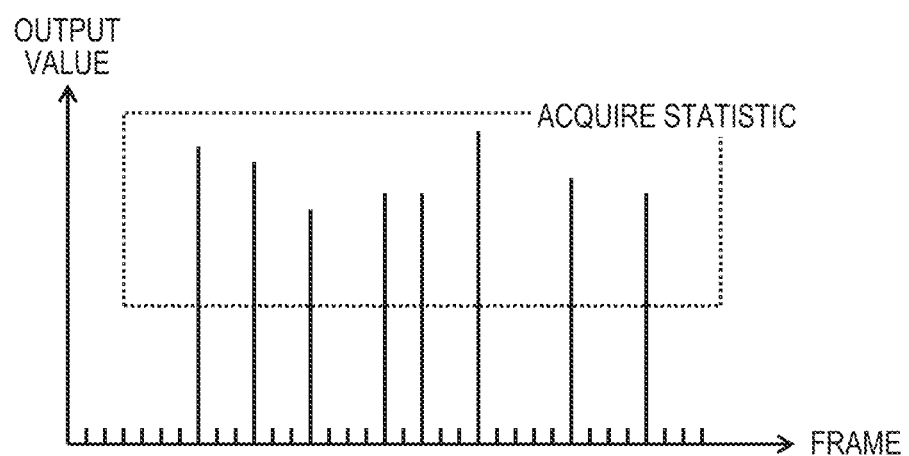
FIG. 8 is a diagram showing a signal output of one pixel included in the radiographic imaging apparatus shown in FIG. 1.

A method for determining a correction coefficient from the statistic of a plurality of acquired signals will now be described. FIG. 8 shows a signal output of one pixel 120 per frame in the radiation photon position determined images shown in FIG. 7B. The horizontal axis represents frame, and the vertical axis represents the value of a signal output from the photodetector of the pixel 120. When the pixel 120 does not detect light generated through conversion of a radiation photon, the output signal value is, for example, 0 (noise level). The processor 103 acquires a plurality of signals (first signals) when light generated through conversion of a radiation photon is detected, and determines a statistic of the plurality of signals. As the statistic, for example, it is possible to use an average value, a median value, a mode value, or the like. The obtained statistic indicates energy sensitivity to the radiation photon incident on the photodetector of the pixel 120. The processor 103 determines a correction coefficient for converting the obtained statistic to a value that corresponds to a predetermined energy value. The processor 103 can acquire a correction coefficient image by determining a correction coefficient for each of the pixels 120 included in the sensor panel 106 based on a statistic.

The amount of data used to determine a statistic increases as the number of times of incidence of a radiation photon on each pixel 120 increases. Accordingly, the processor 103 can acquire a more accurate correction coefficient image. For example, the processor 103 may determine a statistic from a signal output from the photodetector when 100 or more radiation photons are incident on each pixel 120.

Here, the number of radiation photons incident on each pixel 120 can be adjusted by appropriately setting the amount of radiation emitted from the radiation source 101 and the frame rate when imaging is performed on the sensor panel 106. Also, the amount of radiation emitted, and the frame rate may be set so as to avoid a pile-up. As used herein, the term "pile-up" refers to a situation in which a plurality of radiation photons are detected simultaneously by the photodetector of the same pixel 120 on the sensor panel 106, and the plurality of radiation photons are detected as a single radiation photon. In this case, an incorrect correction coefficient may be acquired as a result of the value of a signal output from the photodetector of the pixel 120 having an irregular value that is different from the value generated when one radiation photon is incident. In addition, the resulting radiographic image may have poor image quality due to the value of a signal output from the pixel 120 having an irregular value. In order to avoid such a pile-up, the frame rate may be set such that the number of radiation photons incident on each pixel 120 is one or less during an irradiation period of one frame. For example, the pile-up may be suppressed by reducing the radiation dose and performing high-frame rate imaging. For example, the operating frequency of the pixels 120 may be set to a value within a range from 10 kHz to several MHz (for example, about 100 kHz). Also, for example, the amount of radiation emitted from the radiation source 101 may be set to a value when the tube voltage is set to about 100 kV, and the tube current is set to about 10 mA. Here, it is assumed that the operating frequency of the pixels 120 is, for example, 100 kHz. If light generated by a plurality of radiation photons is incident on the same pixel 120 during a period of 0.01 milliseconds, a pile-up occurs in which the plurality of radiation photons are detected as a single radiation photon.

The statistic may be determined using all signals output from the photodetector when a radiation photon is incident acquired by each pixel 120. Alternatively, the statistic may be determined using the signal values of some of a plurality of acquired signals. For example, the processor 103 may determine the statistic using, among a plurality of acquired signals, a signal that has the highest/lowest value, or remaining signals obtained by removing some signals that have values that are highest from the top/lowest from the bottom. Alternatively, for example, if the distribution of the values of the plurality of acquired signals is a normal distribution, the processor 103 may determine the statistic using signals check grammar value is within a range of 3σ. It is thereby possible to suppress an influence of the value of an irregular signal on the statistic, the irregular signal being caused by, for example, incidence of cosmic rays, or by a direct hit in which an incident radiation photon is detected directly by the photodetector without being converted to light by the scintillator 105. It is also possible to suppress an influence of the value of an irregular signal caused by a pile-up on the statistic.

In the present embodiment, radiation is emitted from the same radiation source 101 in the calibration mode and the imaging mode. However, the calibration mode and the imaging mode may be performed using different radiation sources. For example, in the calibration mode, monochromatic radiation may be emitted, and the photodetector of a pixel 120 may acquire sensitivity to the energy of a radiation photon from an output signal value when light generated through conversion of the radiation photon by the scintillator 105 is detected. In this case, because the energy of radiation incident on each pixel 120 is constant, it is sufficient that one signal is acquired by incidence of a radiation photon. Accordingly, it is unnecessary to determine a statistic. In the photodetector of each pixel 120, by detecting one signal output by incidence of a radiation photon, the processor 103 can determine an accurate correction coefficient, and acquire a correction coefficient image. Accordingly, when determining a correction coefficient, it is unnecessary to, for each pixel 120, acquire signals output from the photodetector when a plurality of radiation photons are incident, and it is therefore possible to significantly reduce the length of time of the calibration mode. As described above, it is possible to use a monochromatic radiation source that contains, for example, a radioactive substance in the calibration mode in which a correction coefficient image is acquired, and use a radiation source 101 that generates radiation through braking radiation in the imaging mode.

Also, for example, radiation of different energy may be emitted, and the processor 103 may determine sensitivities to a plurality of radiation photons of different energy, and acquire a correction coefficient image based on the determined sensitivities. Also, the energy of radiation photons used to acquire a correction coefficient image may be set to a value within a range that is less than or equal to the energy used to capture a subject.

When the sensor panel 106 is irradiated with radiation from the radiation source 101, the intensity of incident radiation, or in other words, the number of incident radiation photons, may be nonuniform between the center portion and the end portion of the sensor panel 106. In the case where the intensity of radiation varies within the plane of the sensor panel, if sensitivity is corrected using the number of radiation photons incident on each pixel as disclosed in Japanese Patent Laid-Open No. 2011-85479, the number of incident radiation photons within the plane of the sensor panel varies, which may reduce the accuracy of correction. However, in the present embodiment, the correction coefficient is determined directly from a signal value corresponding to the energy of an incident radiation photon that is output from each pixel 120. Accordingly, even if the intensity of incident radiation varies within the plane of the sensor panel 106, it is possible to determine a correction coefficient that corresponds to the sensitivity to the energy of a radiation photon incident on each pixel 120. As a result, image degradation of a radiographic image caused by a sensitivity variation between pixels 120 may be suppressed.

Figure 9:
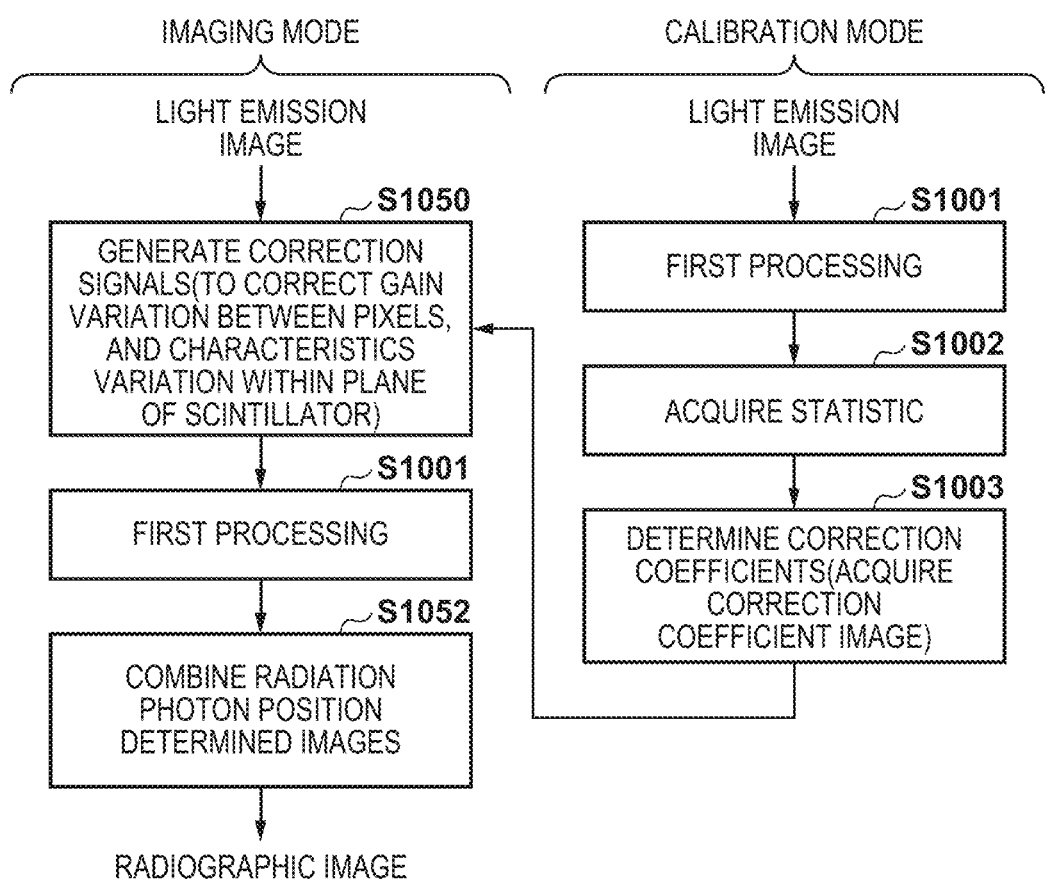
FIG. 9 is a diagram showing an imaging flow performed in the radiographic imaging apparatus shown in FIG. 1.

FIG. 9 shows a flow of radiographic image correction according to the present embodiment. First, in a calibration step performed in the calibration mode, correction coefficients are determined, and an image is acquired. To be specific, the processor 103 performs first processing (S1001) on light emission images acquired without placing a subject between the radiation source 101 and the sensor panel 106, and generates radiation photon position determined images. Next, the processor 103 acquires, for each pixel 120, a plurality of signals output when a radiation photon is incident by using the radiation photon position determined images, and acquires (S1002) a statistic of the plurality of signals. The processor 103 determines (S1003) a correction coefficient for each pixel 120 based on the acquired statistic. The correction coefficients (correction coefficient image) determined in the calibration step are stored in, for example, the memory 130 of the processor 103, and used to generate correction signals when a radiographic image is produced. After a correction coefficient image has been acquired, in an imaging step performed in the imaging mode, correction is performed using the correction coefficient image. The imaging step is an ordinary imaging step performed by placing a subject between the sensor panel 106 and the radiation source 101 that irradiates the sensor panel 106 with radiation. As described above with reference to FIG. 6A, the processor 103 acquires a plurality of light emission images per frame from the imaging portion 104. The processor 103 performs correction on the light emission images by using the correction coefficient image so as to correct a signal output from the photodetector of each pixel 120, and generates (S1050) a correction signal. Through the correction signal generating step, a characteristics variation within the plane of the scintillator 105, and a gain variation between pixels 120 may be corrected. After that, the processor 103 performs first processing (S1001) so as to acquire a plurality of radiation photon position determined images from the correction signals of the light emission images, and combines (S1052) the plurality of radiation photon position determined images. In this way, a radiographic image is generated. Through the radiographic image generating step, a radiographic image as shown in FIG. 6C is obtained.

The correction coefficient may be determined by performing the calibration mode each time a radiographic image is captured. Alternatively, a configuration is possible in which, for example, determined correction coefficients are stored in the memory 130 of the processor 103, and the processor 103 reads out the correction coefficients from the memory 130 when the imaging mode is performed. By determining correction coefficients each time a radiographic image is captured, it is possible to perform appropriate correction each time a radiographic image is captured. Also, by storing correction coefficients in the memory 130, it is unnecessary to perform the calibration mode each time a radiographic image is captured, and thus the time required for imaging can be shortened.

In the present embodiment, an example has been described in which radiographic image correction is performed on the sensor panel 106 that uses indirect conversion elements that use pixels 120 that detect light generated through conversion of radiation photons by the scintillator 105, but the present embodiment is not limited thereto. The radiographic image correction according to the present embodiment is also applicable to an imaging apparatus that uses a sensor panel that includes a direct conversion element that directly detects radiation photons in each pixel.

A radiographic imaging apparatus according to a second embodiment of the present invention will be described with reference to FIGS. 10 to 12. In the first embodiment, a configuration has been described in which a correction coefficient for correcting a variation in sensitivity to a radiation photon incident on each pixel 120 is determined, and in the imaging mode, correction is performed according to the correction coefficients so as to acquire a radiographic image. In the present embodiment, a description will be given of correction for further suppressing image degradation of a radiographic image in a radiographic imaging apparatus that includes indirect conversion elements (photodetectors) that use a scintillator. A radiographic imaging apparatus 100 and a radiographic imaging system 110 may be the same as those of the first embodiment described above.

Figure 10:
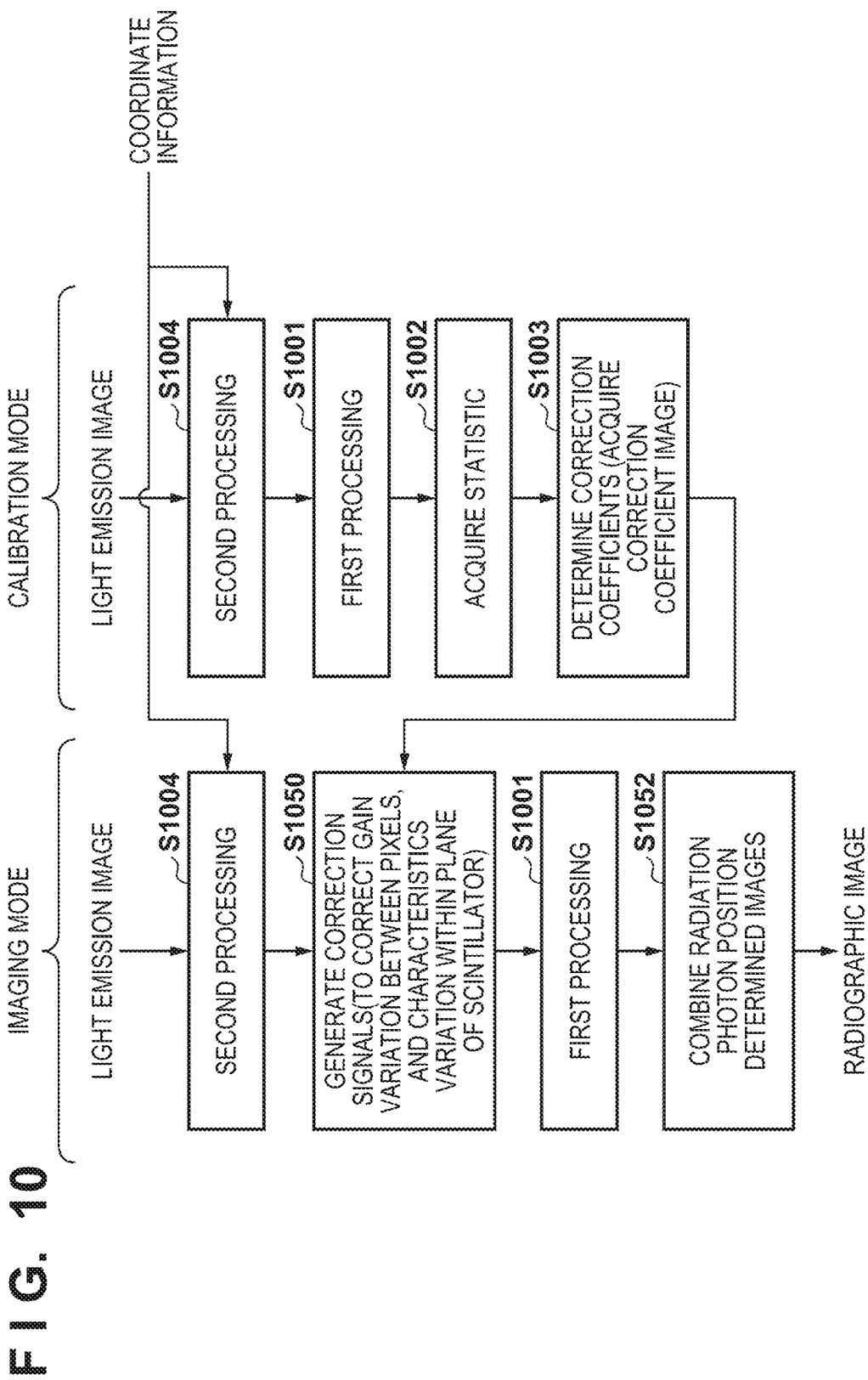
FIG. 10 is a diagram showing a variation of the imaging flow shown in FIG. 9.

FIG. 10 shows a flow of radiographic image correction for suppressing image degradation of a radiographic image by performing correction on a defective pixel caused by at least one of the scintillator 105 and the photodetector included in each of the pixels 120 provided on the sensor panel 106. The processor 103 first acquires coordinate information that indicates the position of a defective pixel on the sensor panel 106. The coordinate information may be acquired as a result of the processor 103 detecting a defective pixel in the calibration mode. Alternatively, coordinate information of defective pixels detected in advance may be stored in the memory 130 of the processor 103, and the processor 103 may acquire the coordinate information from the memory 130. Next, the processor 103 performs second processing (S1004) in which the signal of the defective pixel is replaced based on a signal output from the photodetector of a pixel 120 that is adjacent to the defective pixel according to the coordinate information.

As used herein, the term "defective pixel" refers to a pixel 120 that provides an anomalous output due to, for example, an electrical failure of the photodetector, the switch element and the like that constitute the pixel 120, a scratch on the surface of the scintillator 105, or the like. For example, a pixel 120 that outputs a signal that has a value exceeding a predetermined threshold value may be defined as the defective pixel. Alternatively, for example, a pixel 120 check grammar output signal value is significantly different from a signal value of an adjacent pixel 120 may be defined as the defective pixel. Alternatively, for example, a pixel 120 check grammar output signal value has a low linearity with respect to a change in the intensity of incident light may be defined as the defective pixel. Alternatively, for example, a pixel 120 that does not output a signal at all (that constantly outputs a noise level signal value) due to a disconnection of a circuit that constitutes the pixel 120, or the like may be defined as the defective pixel.

The defective pixel may be detected by performing imaging by irradiating the sensor panel 106 with light before the scintillator 105 is mounted on the sensor panel 106. Alternatively, the defective pixel may be detected by performing imaging without irradiating the sensor panel 106 with light before the scintillator 105 is mounted on the sensor panel 106. In an image captured without irradiation with light, a pixel that outputs a signal indicating light has been detected may be defined as the defective pixel. The coordinate information of defective pixels detected before the scintillator 105 is mounted is stored in the memory 130 of the processor 103.

Also, the defective pixel detection may be performed after the scintillator 105 has been mounted on the sensor panel 106. In this case, in the calibration mode, the processor 103 may detect a defective pixel. The coordinate information of the detected defective pixel may be stored in the memory 130. For example, the processor 103 may detect a defective pixel by performing imaging with or without irradiation with radiation, and using a signal output from the photodetector of each pixel 120. Alternatively, the processor 103 may detect a defective pixel by, for example, causing the radiographic imaging apparatus 100 to perform operations similar to those performed by an integral type radiographic imaging apparatus. That is, the processor 103 may detect a defective pixel from the total amount of electric charges generated as a result of a plurality of radiation photons being incident on each pixel 120 by irradiating the radiographic imaging apparatus 100 with radiation from the radiation source 101. An advantage of defective pixel detection using radiation performed after the scintillator 105 has been mounted on the sensor panel 106 is that it is possible to detect a defective pixel caused after the scintillator 105 has been mounted. The surface of the scintillator 105 has irregularities, and thus a defective pixel may be generated when the scintillator 105 is attached to the sensor panel 106 on which pixels 120 have been formed. When defective pixel detection is performed using radiation, a more accurate defective pixel detection may be possible as compared with the case where defective pixel detection is performed using light before the scintillator 105 is mounted.

Also, the second processing (S1004) may be performed using coordinate information of defective pixels detected under a plurality of conditions. For example, two coordinate information: coordinate information of defective pixels detected by capturing through irradiation with light; and coordinate information of defective pixels detected by capturing without irradiation with light before the scintillator 105 is mounted may be combined as single coordinate information. Alternatively, the second processing (S1004) may be formed using, for example, two coordinate information: coordinate information before the scintillator 105 is mounted and coordinate information after the scintillator 105 is mounted.

By using the coordinate information described above, the processor 103 performs second processing (S1004) in which the signal of a defective pixel is replaced based on a signal output from the photodetector of a pixel 120 that is adjacent to the defective pixel according to the coordinate information. For example, the signal of a defective pixel may be replaced by a signal value from the photodetector of a pixel 120 that is adjacent to the defective pixel, or may be replaced by an average value of the signals from the photodetectors of a plurality of pixels 120 that are adjacent to the defective pixel. In the calibration mode, the processor 103 determines (S1003) a correction coefficient by using the signal of a defective pixel that has undergone replacement through the second processing S1004 on the light emission image. Also, in the imaging mode, the processor 103 generates (S1050) a correction signal by performing correction according to the correction coefficient on the signal of a defective pixel that has undergone replacement through the second processing S1004 in light emission images. After that, the processor 103 performs first processing S1001 so as to acquire a plurality of radiation photon position determined images. Then, the processor 103 generates a radiographic image by combining (S1052) the plurality of radiation photon position determined images. The accuracy of the first processing S1001 is improved by replacing the signal of a defective pixel before the first processing S1001 is performed, and the image degradation of the resulting radiographic image is suppressed.

Figure 11:
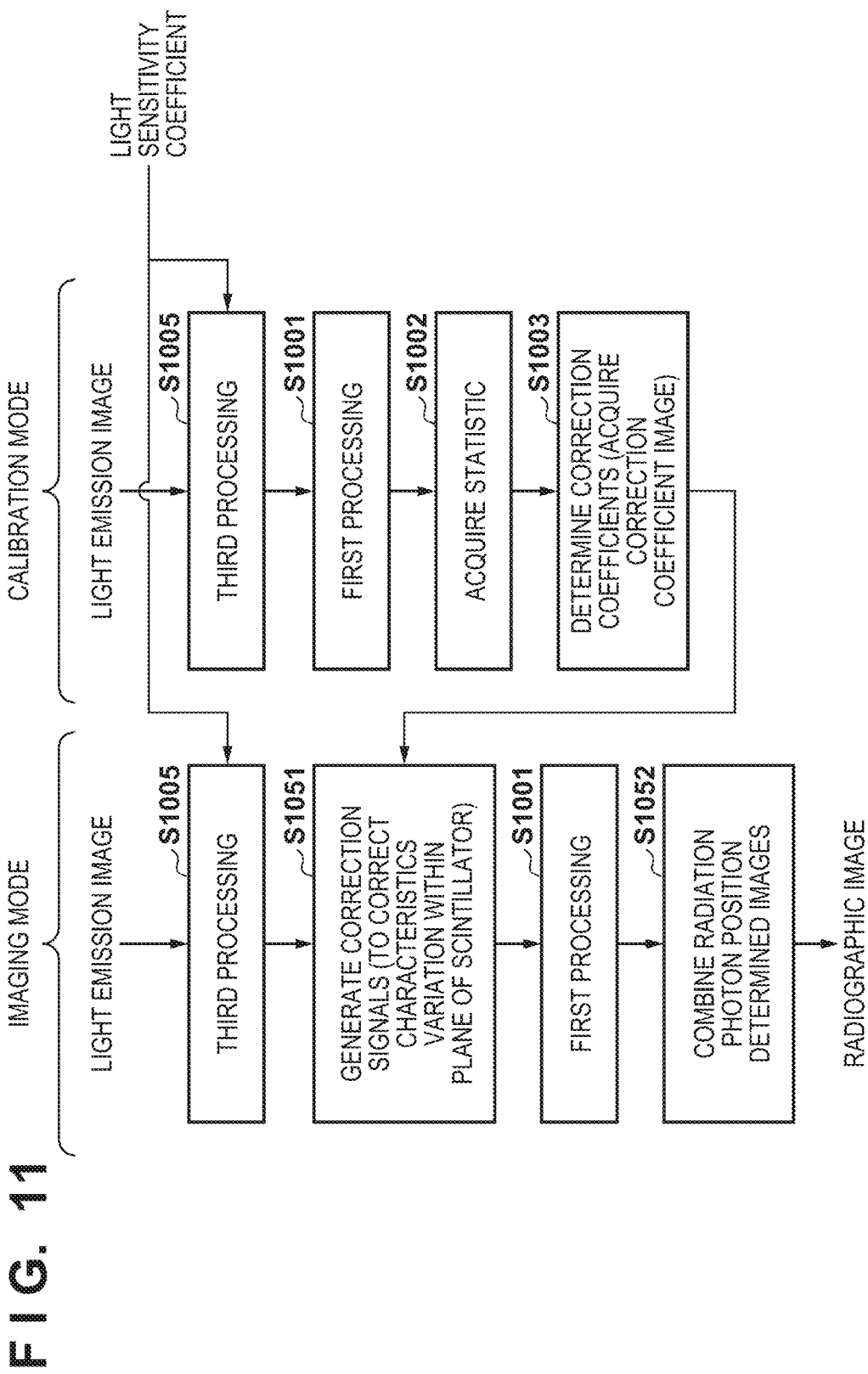
FIG. 11 is a diagram showing a variation of the imaging flow shown in FIG. 9.

Next, FIG. 11 shows a flow of radiographic image correction in which the processor 103 performs third processing S1005 of correcting a signal output from the photodetector provided in each pixel 120 according to a light sensitivity coefficient. The sensor panel 106 is irradiated with light that has a predetermined intensity before the scintillator 105 is mounted on the sensor panel 106. As used herein, the term "light sensitivity coefficient" refers to a coefficient for converting a signal value output from the photodetector of each pixel 120 at this time to a value that corresponds to when light that has a predetermined intensity is incident. That is, the light sensitivity coefficient represents the relationship between the intensity of light incident on the photodetector of a pixel 120 and the value of an optical signal output from the photodetector of the pixel 120. As used herein, the term "value that corresponds to when light that has a predetermined intensity is incident" may be a designed value of the single output from the photodetector of each pixel 120 according to the intensity of incident light. The processor 103 corrects, using the light sensitivity coefficient, a variation in gain of the signal output according to the intensity of light incident on each pixel 120. The light sensitivity coefficients of pixels 120 acquired before the scintillator 105 is mounted on the sensor panel 106 are stored in, for example, the memory 130 of the processor 103. In the present embodiment, the light sensitivity coefficient, the above-described correction coefficients, coordinate information, and the like are stored in the same memory 130, but may be stored in memories that are separately prepared. Also, in the first embodiment and the present embodiment, the memory 130 is provided within the processor 103, but may be provided outside of the processor 103.

In the calibration mode, the processor 103 performs third processing S1005 on light emission images using the light sensitivity coefficients, and corrects the gain of the signal from the photodetector of each pixel 120. After the third processing S1005, correction coefficients are determined (S1003) using signals on which the first processing S1001 has been performed. Also, in the imaging mode, the processor 103 performs correction according to the correction coefficients on the signals corrected through the third processing S1005 performed on the light emission images, and generates (S1051) a correction signal. Because the gain variation between pixels 120 is corrected through the third processing S1005 that uses the light sensitivity coefficients, through the correction signal generation S1051, primarily, a characteristics variation within the plane of the scintillator 105 may be corrected. After that, the processor 103 performs first processing S1001 so as to acquire a plurality of radiation photon position determined images, and generates a radiographic image by combining (S1052) the plurality of radiation photon position determined images. The accuracy of the first processing S1001 is improved by performing the third processing S1005 for correcting the gains of pixels 120 before the first processing S1001 is performed, and the image degradation of the resulting radiographic image can be suppressed.

Figure 12:
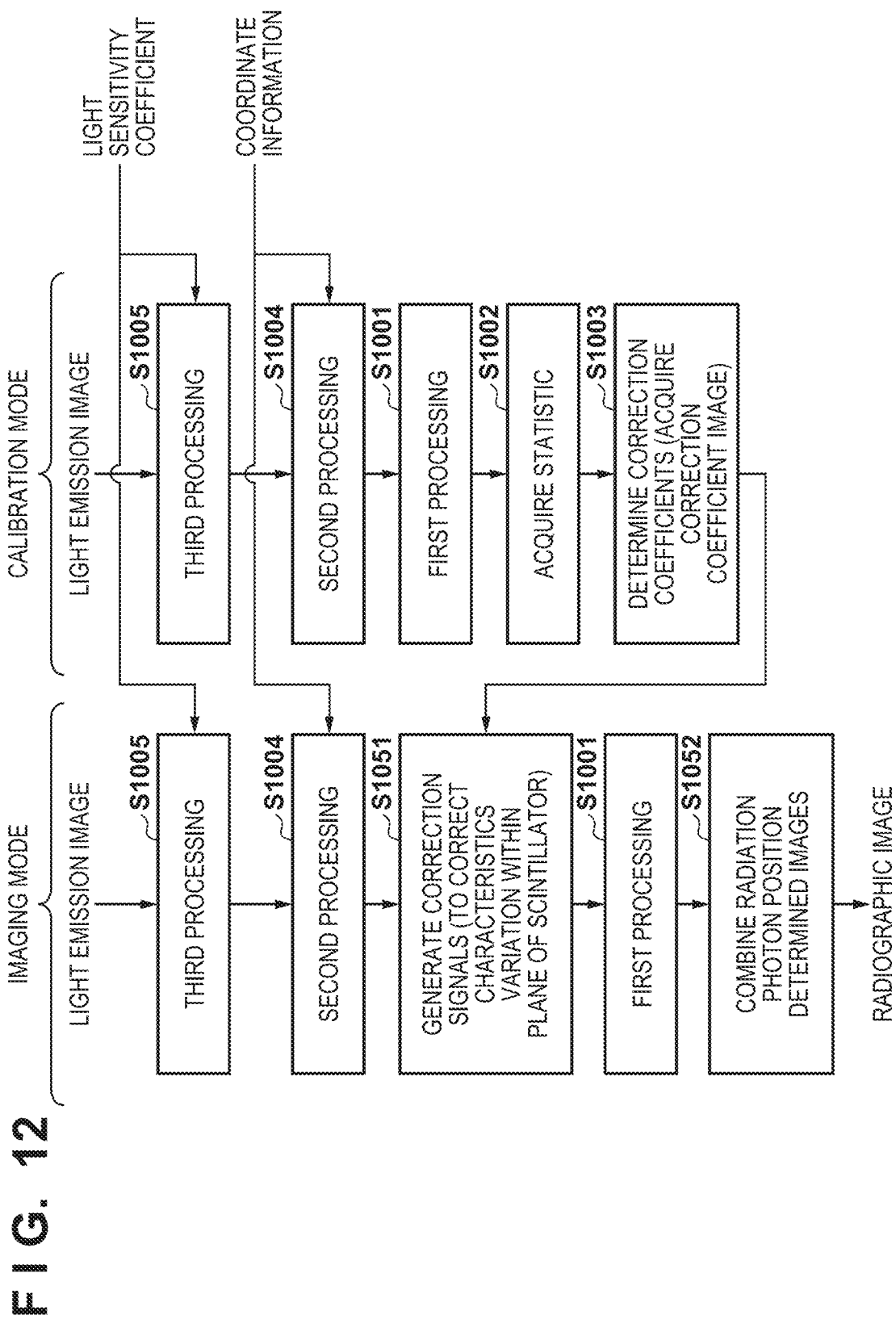
FIG. 12 is a diagram showing a variation of the imaging flow shown in FIG. 9.

Also, as shown in FIG. 12, it is possible to perform both the second processing S1004 and the third processing S1005. The second processing S1004 and the third processing S1005 may be performed in any order, but it is more effective to perform the third processing S1005 first as shown in FIG. 12. This is because the second processing S1004 of correcting a defective pixel uses the output of a pixel 120 adjacent to the defective pixel when the signal of the defective pixel is replaced. By correcting the gain of each pixel 120 through the third processing S1005 so as to make the light sensitivities of the pixels 120 uniform, a highly accurate correction can be performed in the second processing S1004.

Other Embodiments

As described above, the determination of correction coefficients and the correction using the correction coefficients may be performed entirely on software installed on the processor 103. Alternatively, for example, instead of the software, the determination of correction coefficients and the correction using the correction coefficients may be performed by a circuit provided outside of the sensor panel 106. In this case, for example, the circuit may be a FPGA. Also, among the processing operations performed by the processor 103, for example, at least a portion of the processing performed in the imaging mode may be performed by, instead of software, a circuit provided in each pixel 120. Also, the circuit provided in each pixel 120 may perform not only a portion of the processing performed in the imaging mode, but also at least a portion of the processing performed in the calibration mode. In a pixel 120, for example, a correction signal is generated according to the correction coefficient in a light emission image, and the number of signals indicating that light generated through conversion of radiation has been detected is counted for each level based on the signal value. A radiographic image may be generated based on the number of signals indicating the incidence of a radiation photon counted for each level. It is also possible to perform first processing, second processing, and third processing in each pixel 120. In this case, a memory or the like may be provided in each pixel 120 so as to store the correction coefficient determined in the calibration mode, the coordinate information, the light sensitivity coefficient, and the like.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:
1. A radiographic imaging apparatus, comprising:
a sensor panel providing a plurality of pixels, each pixel including a conversion element configured to detect radiation and using in a shared manner a scintillator that converts radiation to light, each pixel including a photodetector for detecting the light; and
a processor configured to generate an image that corresponds to the number of radiation photons incident on each of the plurality of pixels, wherein
in an imaging mode in which an image is generated by radiation that has passed through a subject, the processor generates a correction signal by correcting a value of a signal output from the conversion element of each of the plurality of pixels according to a correction coefficient for converting the value of the signal output from the conversion element on which a radiation photon was incident to a value that corresponds to an energy value of the radiation photon, and generates an image based on the number of correction signals of pixels on which a radiation photon was incident from among the correction signals of the plurality of pixels,
in a calibration mode in which a radiation photon that has a predetermined energy value is incident on the radiographic imaging apparatus, the processor determines the correction coefficient based on a value of a first signal and a value that corresponds to the predetermined energy value, the first signal being a signal from the conversion element on which a radiation photon was incident among signals output from the conversion element,
the photodetector being configured to output an optical signal that has a value corresponding to an intensity of the light incident on the photodetector, and use the optical signal as a signal output from the conversion element,
the processor is further configured to perform first processing that includes
(i) identifying among the plurality of pixels a group of pixels on which the light was incident during the same period

(ii) determining a pixel above which a radiation photon was incident on the scintillator among the pixels included in the group based on a distribution of the group, and
(iii) for each of the pixels in the group, correcting a value of a signal output from the photodetector of the pixel according to a position at which the radiation photon was incident, and
in the calibration mode the processor performs the first processing on signals output from the photodetectors of the pixels included in the group, and determines the first signals.

2. The radiographic imaging apparatus according to claim 1, wherein the processor is configured to determine a pixel that has output a signal that has a value greater than a predetermined value from its conversion element from among the plurality of pixels as a pixel on which a radiation photon was incident.

3. The radiographic imaging apparatus according to claim 1, wherein in the calibration mode the processor is configured to acquire, for each of the plurality of pixels, a plurality of the first signals, and determine the correction coefficient based on a statistic of the plurality of the first signals.

4. The radiographic imaging apparatus according to claim 3, wherein the processor is configured to use as the statistic, any one of a median value of the plurality of the first signals, a mode value of the plurality of the first signals, and an average value of the plurality of the first signals.

5. The radiographic imaging apparatus according to claim 3, wherein the processor is configured to determine the statistic based on 100 or more of the first signals for each of the plurality of pixels.

6. The radiographic imaging apparatus according to claim 1, wherein the processor performs the first processing on the correction signals in the imaging mode.

7. The radiographic imaging apparatus according to claim 1, wherein the processor acquires coordinate information of a defective pixel caused by at least one of the scintillator and the photodetector,
in the calibration mode the processor performs second processing in which a signal of the defective pixel is replaced based on a signal output from the photodetector of a pixel that is adjacent to the defective pixel according to the coordinate information, and
the processor determines the correction coefficient using the signal of the defective pixel that has undergone replacement through the second processing.

8. The radiographic imaging apparatus according to claim 7, wherein the processor acquires the coordinate information by detecting the defective pixel based on at least one of a signal output from each of the plurality of pixels while irradiation with radiation is performed, a signal output from each of the plurality of pixels without irradiation with radiation, and a total amount of electric charges generated by incidence of a plurality of radiation photons on each of the plurality of pixels through irradiation with radiation.

9. The radiographic imaging apparatus according to claim 7, wherein the processor includes a first memory that stores the coordinate information, and
the processor performs the second processing in accordance with the coordinate information stored in the first memory.

10. The radiographic imaging apparatus according to claim 7, wherein in the imaging mode the processor performs correction according to the correction coefficient on the signal of the defective pixel that has undergone replacement through the second processing.

11. The radiographic imaging apparatus according to claim 1, wherein the processor includes a second memory that stores a light sensitivity coefficient for converting a value of a signal from a photodetector on which light of a predetermined intensity was incident among the plurality of pixels to a value that corresponds to the light of a predetermined intensity,
the processor performs third processing in which a value of a signal output from the photodetector of each of the plurality of pixels is corrected according to the light sensitivity coefficient stored in the second memory, and
in the calibration mode the processor determines the first signal by performing the third processing on a signal output from the photodetector of a pixel on which a radiation photon was incident.

12. The radiographic imaging apparatus according to claim 11, wherein in the imaging mode the processor performs correction according to the correction coefficient on a signal that has been corrected through the third processing.

13. The radiographic imaging apparatus according to claim 1, wherein the same radiation source is used in the calibration mode and the imaging mode to irradiate the sensor panel with radiation.

14. The radiographic imaging apparatus according to claim 1, wherein in the imaging mode, among the correction signals for each of the plurality of pixels, the processor counts, correction signals of pixels on which a radiation photon was incident according to a plurality of levels based on values of the correction signals, and generates a radiographic image based on the number of the correction signals counted according to the plurality of levels.

15. A control method for controlling a radiographic imaging apparatus in order to form an image formed by radiation that has passed through a subject, said radiographic imaging apparatus including a sensor panel in which a plurality of pixels are provided, each pixel including a conversion element configured to detect radiation, the control method comprising:
generating a correction signal by correcting a value of a signal output from the conversion element of each of the plurality of pixels according to a correction coefficient for converting a value of a first signal output from the conversion element on which a radiation photon was incident to a value that corresponds to an energy value of the radiation photon;
generating an image based on the number of correction signals of pixels on which a radiation photon was incident from among the correction signals of the plurality of pixels; and
in a calibration mode in which a radiation photon that has a predetermined energy value is incident on the radiographic imaging apparatus, determining the correction coefficient based on a value of a first signal and a value that corresponds to the predetermined energy value, the first signal being a signal from the conversion element on which a radiation photon was incident among signals output from the conversion element,
the plurality of pixels use in a shared manner a scintillator that converts radiation to light, each pixel including a photodetector for detecting the light,
the photodetector outputs an optical signal that has a value that corresponds to an intensity of the light incident on the photodetector, and uses the optical signal as a signal output from the conversion element, wherein
the control method further performs first processing that includes (i) identifying among the plurality of pixels a group of pixels on which the light was incident during the same period,
(ii) determining a pixel above which a radiation photon was incident on the scintillator among the pixels included in the group based on a distribution of the group, and
(iii) for each of the pixels in the group, correcting a value of a signal output from the photodetector of the pixel according to a position at which the radiation photon was incident, and in the calibration mode, determining the first signals by performing the first processing on signals output from the photodetectors of the pixels included in the group.

16. A non-transitory computer-readable storage medium storing a program for causing a computer to execute a control method for controlling a radiographic imaging apparatus in order to form an image formed by radiation that has passed through a subject, said radiographic imaging apparatus including a sensor panel in which a plurality of pixels are provided, each pixel including a conversion element for detecting radiation, the control method comprising:

generating a correction signal by correcting a value of a signal output from the conversion element of each of the plurality of pixels according to a correction coefficient for converting a value of a first signal output from the conversion element on which a radiation photon was incident to a value that corresponds to an energy value of the radiation photon;

generating an image based on the number of correction signals of pixels on which a radiation photon was incident from among the correction signals of the plurality of pixels; and in a calibration mode in which a radiation photon that has a predetermined energy value is incident on the radiographic imaging apparatus, determining the correction coefficient based on a value of a first signal and a value that corresponds to the predetermined energy value, the first signal being a signal from the conversion element on which a radiation photon was incident among signals output from the conversion element, the plurality of pixels use in a shared manner a scintillator that converts radiation to light, each pixel including a photodetector for detecting the light, the photodetector outputs an optical signal that has a value that corresponds to an intensity of the light incident on the photodetector, and uses the optical signal as a signal output from the conversion element, wherein the control method further performs first processing that includes (i) identifying among the plurality of pixels a group of pixels on which the light was incident during the same period,
(ii) determining a pixel above which a radiation photon was incident on the scintillator among the pixels included in the group based on a distribution of the group, and
(iii) for each of the pixels in the group, correcting a value of a signal output from the photodetector of the pixel according to a position at which the radiation photon was incident, and in the calibration mode, determining the first signals by performing the first processing on signals output from the photodetectors of the pixels included in the group.

* * * * *